(12) United States Patent
Belluscio et al.

(10) Patent No.: US 9,119,972 B2
(45) Date of Patent: Sep. 1, 2015

(54) COMPOSITIONS AND METHOD FOR THERMAL PROTECTION OF HAIR

(75) Inventors: Maryalice Belluscio, Long Valley, NJ (US); William Michael J. Dizon, Los Gatos, CA (US)

(73) Assignee: AKZO NOBEL CHEMICALS INTERNATIONAL B.V., Amersfoort (NL)

( * ) Notice: Subject to any disclaimer, the term of this patent is extended or adjusted under 35 U.S.C. 154(b) by 0 days.

(21) Appl. No.: 13/498,652

(22) PCT Filed: Sep. 28, 2010

(86) PCT No.: PCT/EP2010/064324
§ 371 (c)(1),
(2), (4) Date: Mar. 28, 2012

(87) PCT Pub. No.: WO2011/039160
PCT Pub. Date: Apr. 7, 2011

(65) Prior Publication Data
US 2012/0183485 A1    Jul. 19, 2012

Related U.S. Application Data

(60) Provisional application No. 61/247,719, filed on Oct. 1, 2009.

(30) Foreign Application Priority Data

Oct. 23, 2009    (EP) .................................... 09173911

(51) Int. Cl.
| | |
|---|---|
| *A61Q 5/06* | (2006.01) |
| *A61Q 5/12* | (2006.01) |
| *A61Q 5/00* | (2006.01) |
| *A61Q 5/02* | (2006.01) |
| *A61Q 5/04* | (2006.01) |
| *A61K 8/81* | (2006.01) |

(52) U.S. Cl.
CPC ................ *A61Q 5/00* (2013.01); *A61K 8/8152* (2013.01); *A61K 8/8158* (2013.01); *A61Q 5/02* (2013.01); *A61Q 5/04* (2013.01); *A61Q 5/06* (2013.01); *A61Q 5/12* (2013.01)

(58) Field of Classification Search
CPC ............. A61Q 5/00; A61Q 5/06; A61Q 5/02; A61Q 5/12; A61Q 5/04
USPC ........................... 424/70.11, 70.1, 70.16, 70.2
See application file for complete search history.

(56) References Cited

U.S. PATENT DOCUMENTS

| | | | |
|---|---|---|---|
| 5,362,486 A | 11/1994 | Nandagiri et al. | |
| 5,639,448 A | 6/1997 | Galleguillos et al. | |
| 6,056,946 A | 5/2000 | Crudele et al. | |
| 6,740,317 B1 * | 5/2004 | Cho et al. | 424/70.1 |
| 7,335,348 B2 * | 2/2008 | Giroud et al. | 424/70.1 |
| 2004/0247553 A1 | 12/2004 | Cannell et al. | |
| 2009/0104138 A1 | 4/2009 | Shimatani et al. | |
| 2011/0174329 A1 * | 7/2011 | Seng et al. | 132/206 |

FOREIGN PATENT DOCUMENTS

| | | |
|---|---|---|
| CA | 2 304 574 A1 | 4/1999 |
| EP | 0 524 345 A1 | 1/1993 |
| EP | 0 524 346 A1 | 1/1993 |
| JP | H 069343 A | 1/1994 |
| JP | 2001 518488 A | 10/2001 |
| JP | 2005 314365 | 11/2005 |
| JP | 2008 137916 | 6/2008 |
| JP | 2008 542216 A | 11/2008 |
| WO | 9917719 A1 | 4/1999 |
| WO | WO 02/078649 A2 | 10/2002 |
| WO | 2006 128608 A1 | 12/2006 |
| WO | WO 2008/009907 A1 | 1/2008 |
| WO | WO 2009/102758 A1 | 8/2009 |

OTHER PUBLICATIONS

M.L.Tate, Quantification and prevention of hair damage, Journal of the society of cosmetic chemists, Jun. 22, 1993, pp. 347 and 358.*
Merriam-Webster. Plasticizer. Date retrieved: Dec. 10, 2014.*
Merriam-Webster. Thermoplastic. Date retrieved: Dec. 10, 2014.*
European Search Report for EP Application No. 09173911.0 completion date Jul. 26, 2010.
International Search Report for PCT Application No. EP2010/064324 completion date Mar. 19, 2012.
Abstract for European Publication No. 0 524 345 A1.
"AkzoNobel Polymers Keep Hair Stylish and Fully Protected from Thermal Damage," Oct. 22, 2009(XP002592244) URL:http://www.sofw.com/index/sofw_de-sofwde_produktneuheiten.htm.
English Translation of First Office Action from Chinese Patent Application No. 201080042509.2 mailed Apr. 22, 2013.
English translation of Notice of Reasons for Rejection dated Nov. 28, 2013.
"Straightening Facts : How hot is too hot?" on the website "thenaturalhavenbloom.com", pp. 1-2, May 12, 2009.
K. Gregorski, Adv. Exp. Med. Biol., "Protein Crosslinking," M. Friedman, editor, Plenum Press, New York, 1977, pp. 329-344.
J. Cao, Thermochimica Acta, 335: 5-9 (1999).

* cited by examiner

*Primary Examiner* — Frederick Krass
*Assistant Examiner* — Tracy Liu
(74) *Attorney, Agent, or Firm* — Norris McLaughlin & Marcus, P.A.

(57) ABSTRACT

This invention details a method for providing thermal protection to human hair by applying an aerosolized polymer system to the hair before heat treatment. It has been found that acrylate polymers provide good protection from the damaging affects of curling irons and straightening irons and afford improvements in the look and feel of the treated hair.

11 Claims, 2 Drawing Sheets

Virgin Control (no polymer, no heat treatment)

Magnification 10.00kx

Heat Control (no polymer applied but exposed to 12 heat cycles)

Magnification 10.00kx

AMPHOMER (water)

Magnification 10.00kx

Luviset PUR (water)

Magnification 10.00kx

COMPOSITIONS AND METHOD FOR THERMAL PROTECTION OF HAIR

FIELD OF INVENTION

This invention relates to a novel composition for protecting hair from damage by thermal processes such as curling and straightening devices. A method for applying a polymer system to the hair and the heat treatment of hair containing such polymers is also described.

BACKGROUND OF THE INVENTION

A hair fiber is composed of three major sections: cuticle (the outermost layer), cortex, and medulla. It is well understood that treatments requiring heating the hair by contact with hot surfaces damages the hair fiber. More specifically heating causes significant damage to the cuticle, or outermost layer of the hair shaft. The cuticle is composed of flattened keratinized material that is arranged in a scale like fashion. The cuticle can be further broken down into endocuticle, exocuticle, and epicuticle. For the purpose of this invention we are concerned with the protection of the epicuticle. The epicuticle is a heavily keratinized protein rich structure which is associated with lipids. It is this layer which gives hair the ability to repel water. This is the outermost layer that can be easily damaged by curling and straightening tools. The cuticle scales can be easily damaged, resulting in de-cementation and lifting, vertical cracking, shear band formation, bulges, and craters. All of the types of damage described above result in removal of portions of the cuticle exposing the inner most layers of the hair resulting in split ends, breakage and dullness of the hair fiber. Curling irons and straightening irons that come in direct contact of the hair fiber typically have surface temperatures above 150° C. At these elevated temperatures, the hair cuticle endures a significant amount stress resulting in loss of the cuticle or protective coating, thus resulting in the fiber being more hydrophilic in nature.

With each repeated heating cycle the hair becomes more damaged to the point of splitting, breaking, frizzing or just losing its luster and full body look of healthy hair. Many conditioners are sold commercially to repair or mask the affects of deleterious processes such as curling or straightening, and there is still a very strong need for a method to prevent the damage from occurring.

Currently there are several additive ingredients in the market which claim thermal protection for the hair. These additives range from silicones to plasticizers and some polymeric systems have been used to deliver or carry these materials. However, the majority of these additives can only be used under specific conditions and have poor compatibility with solvents and propellants; therefore, it is difficult to incorporate them in hair styling products such as hairsprays. Aside from additives, there are very few existing polymers which provide thermal protection to a certain extent, but these polymers are not used too often due to their lack of performance or toxicity issues. Accordingly, there still exists a need for a polymeric system that can provide the thermal protection and be applied as a hairspray or styling aid.

SUMMARY OF THE INVENTION

It has now been found that certain polymers systems containing acrylate monomers can stop or at least minimize the damage to hair normally associated with thermal processing. Accordingly, in an aspect of the invention, the invention relates to a method of minimizing cuticle damage to human hair that is subjected to a thermal process of greater than 150° C. The method comprises contacting the hair with an anhydrous alcohol solution of a polymer composition prior to subjecting same to the thermal process. The polymer comprises greater than about 10 weight percent of at least one acrylate monomer, wherein the acrylate monomer is acrylic or methacrylic acid.

In another aspect, the invention is directed to a method for protecting hair from damage when the hair is contacted with a heated surface. The method comprises applying a formulation to the hair prior to contacting same with a heated surface. The formulation comprises an anhydrous alcohol solution of a polymer comprising greater than 10 weight percent of an acrylate monomer wherein the acrylate monomer is acrylic acid or methacrylic acid, and wherein the heated surface has a temperature of greater than about 150° C.

In yet another aspect, the invention relates to a formulation for protecting hair from thermal damage resulting from contacting the hair with a heated surface, wherein the heated surface has a temperature of greater than about 150° C. The formulation contains an anhydrous alcohol solution of a polymer which comprises greater than 10 weight percent of at least one acrylate monomer. The acrylate monomer is acrylic acid or methacrylic acid. The formulation is effective in attaining a wetting force of less than about $4.0 \times 10^{-4}$ mN for the hair subsequent to contacting same with the heated surface.

BRIEF DESCRIPTION OF THE DRAWING

The invention is best understood from the following detailed description when read in connection with the accompanying drawings. Included in the drawings are the following figures.

DESCRIPTION OF THE INVENTION

Figure 1:
FIG. 1 is an SEM image showing a virgin hair fiber with no heat treatment.

As noted above, certain polymer systems containing acrylate monomers have been found that can stop or at least minimize the damage to hair normally associated with thermal processing. For purposes of this invention, thermal processing is any hair treatment where the hair is directly contacted with a hot surface. Some non-limiting examples of these processes are curling irons, and straightening irons. In an embodiment of the invention, the hair is contacted with a heated surface in which the heated surface has a temperature of greater than about 150° C. In another embodiment, the heated surface has or is heated to a temperature greater than about 200° C.

The polymers of this invention can be any type of polymers which is made of or modified to contain an acrylate monomeric repeat unit. The polymers of this invention can be anionic, cationic or amphoteric and non-ionic. Non-limiting examples of acrylate monomers are acrylic acid, methacrylic acid, methylacrylate, methacrylate and the like. In the case where the monomer is acrylic or methacrylic acid, the acid group can be neutralized with typical reagents such as triethanol amine (TEA), AMP, sodium carbonate, sodium hydroxide or the like. In one embodiment of this invention the polymer is a copolymer of acrylate or methacrylate monomers The polymers of this invention can also be used in combination with one or more other polymers typically found in hair care products such as, but not limited to (listed as NCI names) VA/Crotonates/Vinyl Neodecanoate Copolymer, Polyquaternium-55, Acrylates/Octylacrylamide Copolymer, Acrylates/Hydroxyesters Acrylates Copolymer, Acrylates/Octylacrylamide/Diphenyl Amodimethicone Copolymer, Acrylates/C1-2 Succinates/Hydroxyacrylates Copolymer, Octylacrylamide/Acrylates/Butylaminoethyl Methacrylate Copolymer, Polyacrylate-12, Ammonium VA/Acrylates Copolymer, Acrylamide/Sodium Acryloyldimethyltaurate/Acrylic Acid Copolymer, Ethylene/VA Copolymer, Acrylates/Steareth-20 Methacrylate Copolymer, Polyvinyl Acetate, PEG-150/Stearyl Alcohol/SMDI Copolymer, PVP/VA/Itaconic Acid Copolymer, PEG-150/Decyl Alcohol/SMDI Copolymer, Hydrolyzed Wheat Protein/PVP Crosspolymer, VA/Crotonates Copolymer, PVP VP/Methacrylamide/Vinyl Imidazole Copolymer, VP/Acrylates/Lauryl Methacrylate Copolymer, Polyurethane-1, Acrylates/VP Copolymer, Polyacrylate-22 Styrene/VP Copolymer, Polyquaternium-72, Vinyl Caprolactam/VP/Dimethylaminoethyl Methacrylate Copolymer, Hydroxypropyltrimonium Hydrolyzed Corn Starch, Acrylates/Acrylamide Copolymer, Sodium Laneth-40 Maleate/Styrene Sulfonate Copolymer, Acrylates/Amino acrylates/C10-30 Alkyl PEG-20 Itaconate Copolymer, Polyester-5, Acrylates/C10-30 Alkyl Acrylate Crosspolymer, VA/Butyl Maleate/Isobornyl Acrylate Copolymer, Acrylates/C12-22 Alkyl Methacrylate Copolymer, Acrylates/C1-2 Succinates/Hydroxyacrylates Copolymer, Acrylates Copolymer, Isobutylene/Ethylmaleimide/Hydroxyethylmaleimide Copolymer, Acrylates/Vinyl Isodecanoate Crosspolymer, Polyimide-1, Acrylates/Vinyl Neodecanoate Crosspolymer, Butyl Ester of PVM/MA Copolymer, Acrylates/VP Copolymer, PVM/MA Copolymer, Butyl Methacrylate/DMAPA Acrylates/Vinylacetamide Crosspolymer, Stearylvinyl Ether/MA Copolymer, Starch/Acrylates/Acrylamide Copolymer, Isopropyl Ester of PVM/MA Copolymer, VP/Acrylates/Lauryl Methacrylate Copolymer, Polyvinyl Methyl Ether, VP/DMAPA Acrylates Copolymer, Calcium/Sodium PVM/MA Copolymer, VP/Vinyl Caprolactam/DMAPA Acrylates Copolymer, AMP-Acrylates/Allyl Methacrylate Copolymer, Ethyl Ester of PVM/MA Copolymer, Polyacrylate-14, Polyacrylate-2 Crosspolymer, Sodium Polystyrene Sulfonate, Polyurethane-14 (and) AMP-Acrylates Copolymer, Polyurethane-2, Butyl Acrylate/Ethylhexyl Methacrylate Copolymer, and Butyl Acrylate/Styrene Copolymer. The official chemical description of each of these chemical names can be found in the INCI dictionary or at they website (www.ctfa.org).

In an embodiment of the invention, the polymer comprises greater than about 10 weight percent of at least one acrylate monomer. In another embodiment, the polymer comprises greater than 50 weight percent of at least one acrylate monomer. The percent of acrylate monomer in the polymer is defined as a weight percent of the acrylate monomer based on the weight of the total monomer(s) present.

In an embodiment of the invention, the polymer is contacted is damaged. The damage may be measured as a wetting force as defined by the Wetting Force Measurement described below. In an embodiment of the invention, the damage to the hair is measured as an average wetting force of less than about $4.0 \times 10^{-4}$ mN of the hair after the thermal process. In another embodiment, damage is measured as an average wetting force of less than about $3.0 \times 10^{-4}$ mN of the hair.

One aspect of this invention is that the polymer can be sprayed onto the hair. While polymers of the type described herein are typically applied to the hair by spraying, it is novel to apply these polymers to the hair before the hot iron is used. In one embodiment of this invention the polymers are sprayed by a pump onto the hair from a solvent chosen from the group consisting of water, methanol, ethanol, isopropanol, acetone, or methyl acetate. In another embodiment the solvent to be sprayed is water or isopropanol. In yet another embodiment the solvent for spraying is ethanol. Alternatively the formulations can be sprayed by means of a pressurized device containing a propellant (aerosol). In addition to any solvent in the formulation, the polymers must be compatible with the propellants used. In an embodiment of this invention the propellants are chosen from the group consisting of hydrocarbon, dimethyl ether, and 1,1-difluoroethane.

In another embodiment of the current invention the polymer system can be deposited onto the hair from a shampoo formulation. In yet another embodiment the polymer can be deposited onto the hair from a cream rinse formulation. In either of these embodiments the hair can either be dried first and then heat treated or the heat treatment can be accomplished directly on the wet hair.

One skilled in the art would recognize that other ingredients can also be added. Such non-limiting examples are colorants, fillers, pigments, dyes, fragrances, surfactants, plasticizers, sunscreens, emollients.

EXPERIMENTAL

Preparation of Hair Samples and Heat Treatment:

A flat iron configured to the highest heat setting possible and allowed to heat up to operational temperature (approximately 210° C.). A sample hair tress is hydrated in water for 5 minutes and excess water squeezed out of the tress and combed through to relieve any tangles present. A spray solution containing 1% polymer solids is then applied to the tress and then the flat iron is applied to the tress in a vertical motion starting from the top and ending at the bottom, repeating this heating process for 5 minutes. The tress is allowed to cool for 1-2 minutes before applying 1.5 cc of shampoo to the tress. The shampoo is worked in for about one minute and then rinsed with warm tap water for an additional minute to make sure that all excess polymer and shampoo is washed off. Comb through the tress to relieve tangles once again, and then place the tress in a 45° C. oven for 15 minutes to allow the tress to dry completely. Pre-wet the tress once again for 1-2 minutes and then repeat the entire process for 12 cycles.

Wetting Force Measurement:

Once all the samples have been prepared and heat treated, they were then measured in terms of wetting force utilizing the KRUSS K14 tensiometer. The KRUSS K14 contains a microbalance in which it submerges a single fiber of material into a liquid and measures the wetting force of that fiber only during the instance when the fiber breaks the surface of the liquid. The fiber was only submerged to a depth of 3 mm. Within the time of submersion, the KRUSS K14 gathered an average of 400 values in units of mili-newtons (mN) in correspondence to the depth. For each of the 12 tress samples, individualized 1 inch fibers were precisely cut and then measured with the KRUSS K14. In support of statistical purposes, 12 fibers of each sample were tested. The average of all 12 fibers of each sample was calculated.

TABLE 1

Wetting Force Measurements

| Sample # | Polymer (solvent) | Average Wetting Force ($10^{-4}$) mN |
|---|---|---|
| 1 | Control (no heat, no polymer) | −0.6088 |
| 2 | Heat control (no polymer) | 7.93328 |
| 3 | Luviset PUR | 7.34064 |
| 4 | Luviset PUR (water) | 7.33811 |
| 5 | FLEXAN ® II*** | 6.88329 |
| 6 | Mirustyle XHP*** | 6.14537 |
| 7 | Luvimer 100P | 5.41103 |
| 8 | DynamX ® (water) | 4.97542 |
| 9 | DynamX ® | 4.38711 |
| 10 | Luvimer 100P (water) | 3.96864 |
| 11 | AMPHOMER ® (ethanol) | 2.27584 |
| 12 | AMPHOMER ® (water) | 1.45294 |

***Solutions delivered through a pump spray, while all others were delivered through an aerosol The above table shows that the polymers that contain acrylate monomers (samples 10 to 12) have the lowest wetting energies after heat treatment. The lower the wetting energy represents a more hydrophobic hair fiber and less damaged hair cuticle due to the action of the polymer treatment. Less damage to the cuticle relates to better feel, higher sheen and overall smoother hair cuticle.

Specifications

| Trade Name | INC Name |
|---|---|
| AMPHOMER ® | Octylacrylamide/Acrylates/Butylaminoethyl Methacrylate Copolymer |
| DynamX ® | Polyurethane-14 (and) AMP-Acrylates Copolymer |
| FLEXAN ® II | Sodium Polystyrene Sulfonate |
| Luvimer 100P | Acrylates Copolymer |
| Luviset P.U.R. | Polyurethane - 1 |
| Mirustyle XHP | Aqua (and) Sodium Laneth-40 Maleate/Styrene Sulfonate Copolymer |

Qualatative Analysis (SEM)

Twelve hair tresses were formed from the same lot of hair for control purposes. Each hair tress was labeled correspondingly to the labels associated with the formulations listed above. The polymers that have been aerosolized were formulated in two different systems: one containing all water and the other containing all ethanol. This was done as a control to determine whether the polymers would perform differently in various solvent environments. Representative SEMs are shown in FIGS. 1-4 to illustrate the visual damage associated with thermal processing.

Virgin Control (No Polymer, No Heat Treatment)

The first SEM image as shown in FIG. 1 is the virgin hair fiber with no heat treatment. From this photomicrograph it can be seen that the hair used for this study was in relatively good condition prior to being used for testing. This photo shows the cuticle having a nice uniform scale-like structure. This can be used a baseline photo to compare the rest of the micrographs for damage.

Heat Control (No Polymer Applied but Exposed to 12 Heat Cycles)

Figure 2:
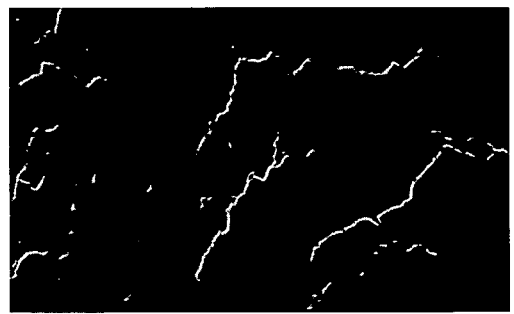
FIG. 2 is an SEM image showing an untreated virgin hair fiber after 12 heat cycles.

The photomicrograph of FIG. 2 shows extensive damage and loss of the cuticle. Portions of the cuticle are broken off while other areas show thermal cracks and craters. The jagged edges and pitting are also representative of the damage done by the heating process. It is the presence of these flakes, cracks and pitting that causes the increase in wetting energy and loss of desirable aesthetics.

Amphomer (Water)

Figure 3:
FIG. 3 is an SEM image showing a virgin hair fiber treated with a polymer composition according to an embodiment of the present invention after heat treatment.

FIG. 3 is a photomicrograph of a sample showing the cuticle with minimal damage and maintained uniform scale like structure of the hair fiber. This represents the protection that would be obtained with acrylate containing polymers of this invention.

Luviset PUR (Water)

Figure 4:
FIG. 4 is an SEM image showing a virgin hair fiber treated with a polymer composition not according to an embodiment of the present invention after heat treatment.

The photomicrograph of FIG. 4 shows the cuticle with the melted polymer attached, yet there is still pitting and damage to the cuticle observed. The presence of the melted polymer, even after shampooing, will leave the hair feeling plastic and un-natural.

FIGS. 1-4 represent Scanning Electron Microscope (SEM) images of the surface of a single fiber of each tress sample in which polymer and heat have been applied to. All the images presented above are shown at a 10,000× magnification. The purpose for these images was to obtain a correlation between the condition of the cuticle and the quantitative data obtained through wetting force analysis shown previously. Hair samples were taken from the same hair tresses that were treated for the wetting force analysis.

Although the invention is illustrated and described herein with reference to specific embodiments, the invention is not intended to be limited to the details shown. Rather, various modifications may be made in the details within the scope and range of equivalents of the claims and without departing from the spirit of the invention.

We claim:

1. A method of minimizing cuticle damage to human hair that is subjected to a hot surface having a temperature of greater than 150° C., said method comprising spraying said hair with a thermal protection formulation effective to minimize said cuticle damage at said temperature and thereafter subjecting said hair to said hot surface, said thermal protection formulation comprising as the only thermal protection agent (A) a thermally protective amphoteric acrylate polymer in (B) a solvent selected from the group consisting of an anhydrous alcohol, water, acetone and methyl acetate, wherein said thermally protective amphoteric acrylate polymer comprises greater than about 10 weight percent of at least one acrylate monomer, wherein the acrylate monomer is acrylic or methacrylic acid, and wherein said thermal protection formulation is effective in attaining an average wetting force of less than $4.0 \times 10^{-4}$ mN after being subjected to the hot surface.

2. The method of claim 1 wherein the hot surface is heated to greater than about 200° C.

3. The method of claim 1 wherein the hot surface is in the form of a curling iron or straightening iron.

4. A method for protecting hair from damage when said hair is contacted with a heated surface, said method comprising spraying said hair with a thermal protection formulation effective to protect said hair from said damage due to said heated surface and thereafter contacting said hair with a heated surface, said thermal protection formulation comprising as the only thermal protection agent (A) a thermally protective amphoteric acrylate polymer in (B) a solvent selected from the group consisting of an anhydrous alcohol, water, acetone and methyl acetate, wherein said thermally protective amphoteric acrylate polymer comprises greater than 10 weight percent of an acrylate monomer, wherein said acrylate monomer is acrylic acid or methacrylic acid, wherein said heated surface has a temperature of greater than 150° C., wherein the thermal protection formulation is effective in attaining an average wetting force of less than about $4.0 \times 10^{-4}$ mN after being subjected to the heated surface.

5. The method of claim 4 wherein the average wetting force is less than about $3.0 \times 10^{-4}$ mN.

6. The method of claim 4 wherein the polymer comprises Octylacrylamide/Acrylates/Butylaminoethyl Methacrylate Copolymer.

7. The method of claim 1 wherein the anhydrous alcohol is selected from the group consisting of methanol, ethanol and isopropanol.

8. The method of claim 4 wherein the anhydrous alcohol is selected from the group consisting of methanol, ethanol and isopropanol.

9. The method of claim 1 wherein the polymer comprises Octylacrylamide/Acrylates/Butylaminoethyl Methacrylate Copolymer.

10. The method of claim 1 wherein the thermal protection formulation further comprises one or more additional ingredients selected from the group consisting of hair care polymers, colorants, fillers, pigments, dyes, fragrances, surfactants, plasticizers, sunscreens and emollients.

11. The method of claim 4 wherein the thermal protection formulation further comprises one or more additional ingredients selected from the group consisting of hair care polymers, colorants, fillers, pigments, dyes, fragrances, surfactants, plasticizers, sunscreens and emollients.

* * * * *